United States Patent
Deriche

(10) Patent No.: US 8,375,579 B2
(45) Date of Patent: Feb. 19, 2013

(54) SYSTEM FOR INJECTING A THERMOPLASTIC MATERIAL

(75) Inventor: Eric Deriche, Mery (FR)

(73) Assignee: Runipsys Europe, Mery (FR)

( * ) Notice: Subject to any disclaimer, the term of this patent is extended or adjusted under 35 U.S.C. 154(b) by 71 days.

(21) Appl. No.: 13/132,218

(22) PCT Filed: Dec. 7, 2009

(86) PCT No.: PCT/EP2009/066508
§ 371 (c)(1),
(2), (4) Date: Jun. 1, 2011

(87) PCT Pub. No.: WO2010/066671
PCT Pub. Date: Jun. 17, 2010

(65) Prior Publication Data
US 2011/0236526 A1    Sep. 29, 2011

(30) Foreign Application Priority Data

Dec. 9, 2008 (FR) ...................................... 08 58394

(51) Int. Cl.
*B29C 45/23* (2006.01)
(52) U.S. Cl. ............................ 29/879; 425/564; 425/572
(58) Field of Classification Search ................... 425/562, 425/563, 564, 565, 566, 572; 29/879
See application file for complete search history.

(56) References Cited

U.S. PATENT DOCUMENTS

| | | | |
|---|---|---|---|
| 4,013,393 A * | 3/1977 | Gellert | ........................... 425/566 |
| 4,712,995 A | 12/1987 | Basnett | |
| 5,162,125 A | 11/1992 | Akselrud et al. | |
| 2005/0238748 A1 | 10/2005 | Jenko | |
| 2009/0194910 A1 | 8/2009 | Rosner et al. | |

FOREIGN PATENT DOCUMENTS

| | | |
|---|---|---|
| EP | 1 447 199 | 8/2004 |
| FR | 2 821 010 | 8/2002 |
| FR | 2 831 644 | 5/2003 |
| WO | WO 2007/006899 | 1/2007 |
| WO | WO 2007/051857 | 5/2007 |

OTHER PUBLICATIONS

English Translation of the Internatinal Preliminary Report on Patentability, issued Jun. 14, 2011, incorporating the English Translation of the Written Opinion of the ISA, ISA/EP, mailed May 10, 2010.

* cited by examiner

*Primary Examiner* — Tim Heitbrink
(74) *Attorney, Agent, or Firm* — Harness, Dickey & Pierce, P.L.C.

(57) ABSTRACT

The disclosure relates to a system for injecting a thermoplastic material in the fluid state, including: a dispenser adapted to be maintained at an injection temperature higher than the temperature limit at which the material is in a fluid state; an injection nozzle defining at least one portion of a transition passage; a stopper mounted inside the transition passage so as to slide between a blocking position and an opening position thereof; and control means for alternately sliding the stopper, wherein the control means comprises a jack with a rod parallel to the sliding direction of the stopper, and which is secured in an offset manner on the dispenser via a flattened beam, and a lever arranged so as to tilt about an axis so as to transmit the movements of the jack rod to the stopper.

20 Claims, 5 Drawing Sheets

SYSTEM FOR INJECTING A THERMOPLASTIC MATERIAL

CROSS-REFERENCE TO RELATED APPLICATIONS

This application is a National Phase Entry of International Application No. PCT/EP2009/066508, filed on Dec. 7, 2009, which claims priority to French Patent Application Serial No. 0858394, filed on Dec. 9, 2008, both of which are incorporated by reference herein.

FIELD OF THE INVENTION

The present invention relates to a system for injecting thermoplastic material into a molding cavity, and a method for manufacturing such a system.

BACKGROUND

An injection system of the "hot runner" type usually includes:
 a manifold delimiting a distribution channel for thermoplastic material and including a thermoplastic material outlet,
 an injection nozzle defining at least a portion of a transit passage the entrance whereof is fluidically connected with the outlet of the distribution channel, and the outlet whereof opens substantially into the mold cavity,
 a nozzle gate mounted so as to slide longitudinally within the transit passage and alternately occupying a position closing said passage and a position opening it,
 control means for causing the nozzle gate to slide alternately between the closing position and the opening position. The control means typically include a power cylinder connected to the nozzle gate. This type of injection system additionally includes supply means capable of supplying the manifold with material to be injected.

To satisfactorily inject the material into the cavity, the material must be maintained in the fluid state, this state being obtained when the material is brought to a predetermined final temperature greater than the temperature of the ambient air. To this end, the manifold includes, in known fashion, means allowing the temperature thereof, and consequently that of the material passing through its distribution channel, to be maintained at a temperature greater than the fusion temperature of the material. The material in the fluid state is inserted into the distribution channel by the supply means and enters the transit passage of the injection nozzle.

When the control means bring the nozzle gate into the closing position, the nozzle outlet is closed and the material to be injected is retained in the transit passage. When the control means bring the nozzle gate into the open position, the nozzle outlet is open and the material is injected into the cavity. Conventionally, said control means are located in the ambient air on the face of the manifold longitudinally opposite to the molding cavity (or "back face" of the manifold).

Now, as the manifold is maintained at an elevated temperature, it is indispensable to provide cooling for the power cylinder. This cooling is typically obtained by means of water circulation around the power cylinder. Now the placement of this water circuit is problematic because it complicates the injection system and is relatively costly. In addition, the thickness of the power cylinder contributes to a considerable increase in thickness of the injection system.

One of the objects of the invention is therefore to design an injection system in which the cooling of the nozzle gate control means can be dispensed with. Another object of the invention is to minimize the total thickness of the injection system.

SUMMARY

According to the invention, a system is proposed for the injection of a thermoplastic material in the fluid state into a molding cavity, comprising:
 a manifold designed to be maintained at an injection temperature greater than the final temperature above which the material occurs in the fluid state, said manifold including a distribution channel and at least one thermoplastic material outlet,
 an injection nozzle defining at least one portion of a transit passage the entrance whereof is fluidically connected with the outlet of the distribution channel, and the outlet whereof opens substantially into the molding cavity,
 a nozzle gate mounted within the transit passage so as to slide between a position closing same and a position opening same,
 control means to cause the nozzle gate to slide alternately, said system being characterized in that said control means include a power cylinder the rod whereof is parallel to the sliding direction of the nozzle gate, secured in offset fashion to the manifold through a flattened beam, and a lever arranged to tilt about a trunnion so as to transmit to the nozzle gate the movements of the power cylinder rod.

Particularly advantageously, said beam carries the tilting trunnion of the lever.

According to a first embodiment of the invention, the beam is a solid, or monobloc, part. Thus it has high stiffness which allows it to satisfy the fatigue life requirement of a system for the injection molding in mass production (that is typically more than 200,000 parts).

According to a second embodiment of the invention, the beam is made up of an assembly of sheet steel parts. This design offers a good compromise between cost and stiffness for a less intensive use of the limited series kind.

According to other features of this embodiment, taken separately or in combination:
 said beam comprises two parallel arms, a cylinder flange mounting secured to the power cylinder and a nozzle gate mounting secured to the manifold;
 the arms and the nozzle gate and cylinder mounts have complementary cutouts allowing them to interlock;
 the arms and the nozzle gate mount have cutouts allowing them to be centered on the nozzle base;
 the lever comprises two sheet steel arms;
 the thickness of the sheet metal parts lies between 2 and 10 mm, preferably between 3 and 5 mm.

The invention also relates to a device for controlling the sliding of a nozzle gate for an injection nozzle, particularly for an injection system as described previously, said device being characterized in that it comprises:
 a flattened beam to secure the power cylinder in an offset position on the manifold, and
 a lever arranged to rock about a trunnion so as to transmit to the nozzle gate the movements of the power cylinder rod.

Another object of the invention relates to a manufacturing method for a system according to the second embodiment described above, comprising the following steps:
 (a) cutting out and if necessary bending the parts comprising the beam,
 (b) assembly of said parts and of the lever,
 (c) securing the assembly to the power cylinder and the manifold.

Advantageously, step (a) also includes cutting out the lever arms. Preferably, step (a) includes laser cutting. Finally, step (b) is advantageously carried out by interlocking the parts.

BRIEF DESCRIPTION OF THE DRAWINGS

Other features and advantages of the invention will appear in the detailed description that will follow, with reference to the appended drawings in which.

DETAILED DESCRIPTION OF THE INVENTION

An injection system according to the invention includes a power cylinder controlling the nozzle gate which is not directly secured to the manifold, but rather offset with respect thereto, through a beam. This installation has a dual advantage. The first is to reduce the total thickness of the system on the order of about one-third. Indeed, the power cylinder is thus housed in a recess and only the thickness of the beam connecting the cylinder with the manifold contributes to the thickness of the system.

In addition, the cylinder no longer being located in contact with the hot manifold, the water cooling which is necessary in the prior art arrangement can be dispensed with. Furthermore, the materials and thicknesses of the beam are designed to allow dissipation of the heat.

Figure 1:
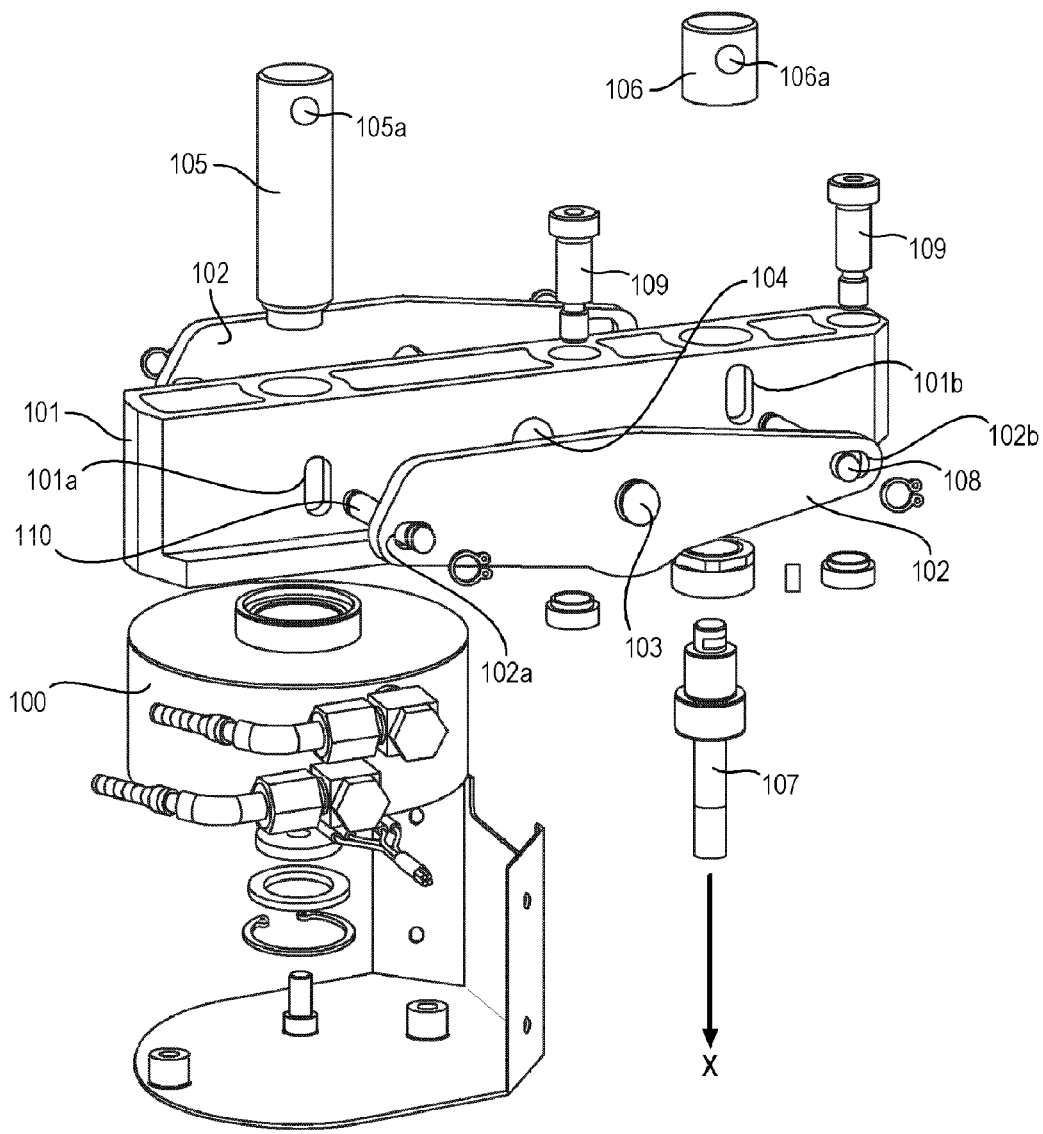
FIG. 1 is an exploded view of the control means for the nozzle gate according to the first embodiment of the invention particularly suited to intensive use of the mass production kind.

According to one basic embodiment of the invention, the control means of the nozzle gate include, with reference to FIG. 1:

a power cylinder 100, secured in an offset fashion to the manifold by means of a beam 101 having a flattened shape, two substantially symmetrical lever arms 102, arranged on either side of the beam 101, and mounted on same so as to allow rocking by means of a trunnion 103 inserted into a through-bore 104 located substantially midway along the length of the beam 101, a power cylinder head 105 mounted on the power cylinder 100 and movable in translation in a direction parallel to the nozzle gate motion direction X, a nozzle gate head 106 rigidly connected to the nozzle gate 107.

The attachment of the cylinder 100 to the beam 101 is provided by any known means, such as screws (not shown in FIG. 1). The movements of the cylinder head 105 are transmitted to the nozzle gate head through the lever arms 102. Indeed, the cylinder head 105 and the nozzle gate head 106 are each drilled with a single bore 105*a*, 106*a* respectively, through which passes a trunnion 110, 108 respectively.

The trunnions 110 and 108 respectively pass through the beam 101 at the two oblong holes 101*a*, 101*b*, and each of the lever arms 102 at the two oblong holes 102*a*, 102*b*. At its end opposite to the power cylinder 100, the beam 101 is secured to the manifold by two screws 109. Thus, when the cylinder imposes an upward translation of the cylinder head 105 (in the configuration of FIG. 1), the levers 102 tilt about the trunnion 103 and drive the nozzle gate head 106 in downward translation, and bring about the closing of the nozzle. Conversely, downward translation of the cylinder head 105 drives the nozzle gate head 106 in upward translation, and thus allows the opening of the nozzle.

The beam 101 has a flattened shape, that is its length is greater than its height and its height is less than or equal to the height of the power cylinder. By way of a non-limiting example, the beam 101 illustrated in FIG. 1 has a height on the order of 40 mm, a length of about 200 mm and a width of about 40 mm. It is associated for example with a hydraulic cylinder having a height of about 40 mm.

To obtain sufficient stiffness and a durability compatible with the life expectancy of the injection system, the beam 101 can be made by machining a block of steel. It is noted that the steel can undergo surface or in-depth treatment with a view to improving its properties. According to another embodiment, the beam 101 can be made in a foundry, of cast iron or steel, the material possibly also undergoing any appropriate treatment.

These embodiments in which the beam is solid, that is made in a single piece, are particularly suitable when the injection system is intended for mass production (that is intended to carry out more than 200,000 injection cycles). Indeed, such a beam is suited to satisfying the fatigue life specification for the intended number of cycles. In addition, in constantly seeking cost reduction, particularly in the case of the manufacture of small quantities of parts (that is ranging typically from 1000 parts (prototypes) up to 200,000 parts (limited series)), for which the cost of the mold has a considerable impact on the cost of the parts, a new beam design, intended to reduce the cost of the beam, has been defined.

Figure 2:
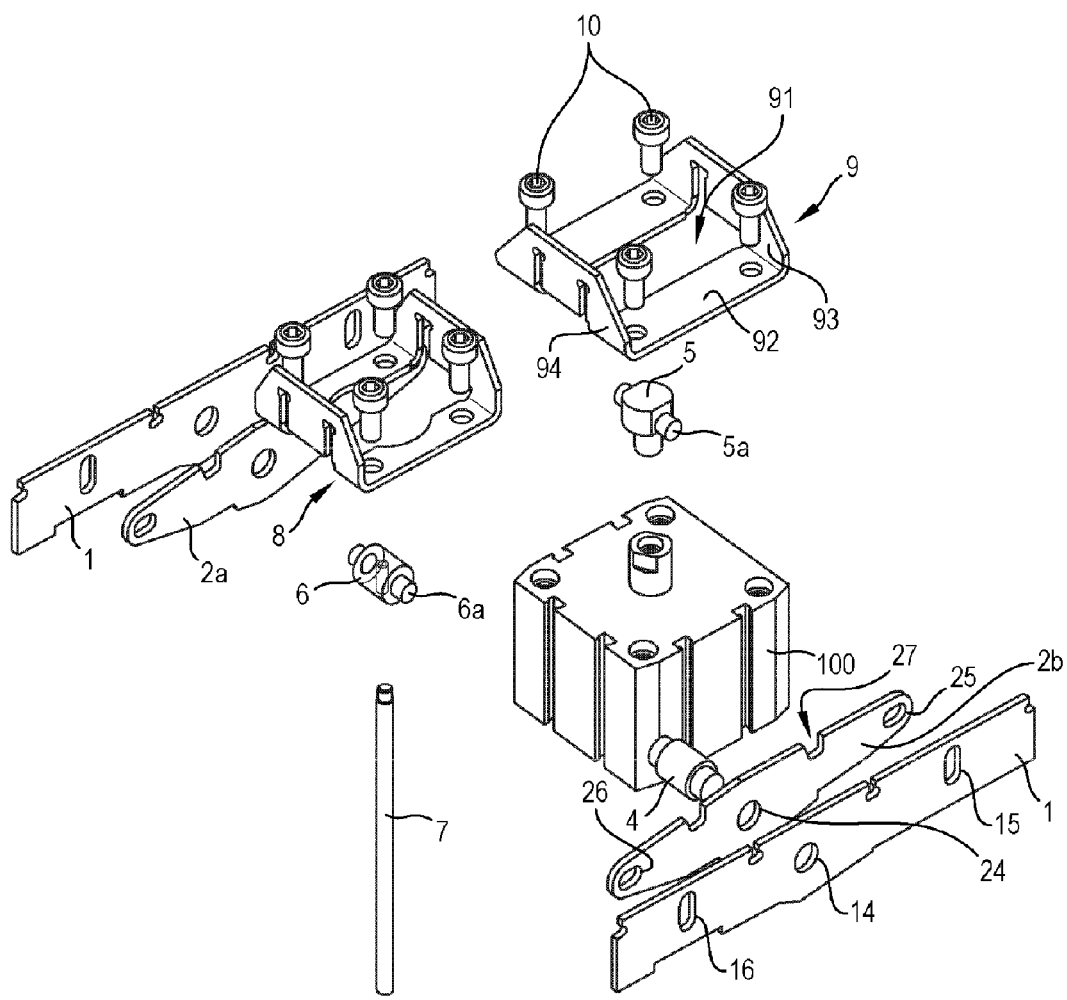
FIG. 2 is an exploded view of control means according to a second embodiment of the invention preferably intended for a less intensive use of the prototype or limited series kind.
Figure 3:
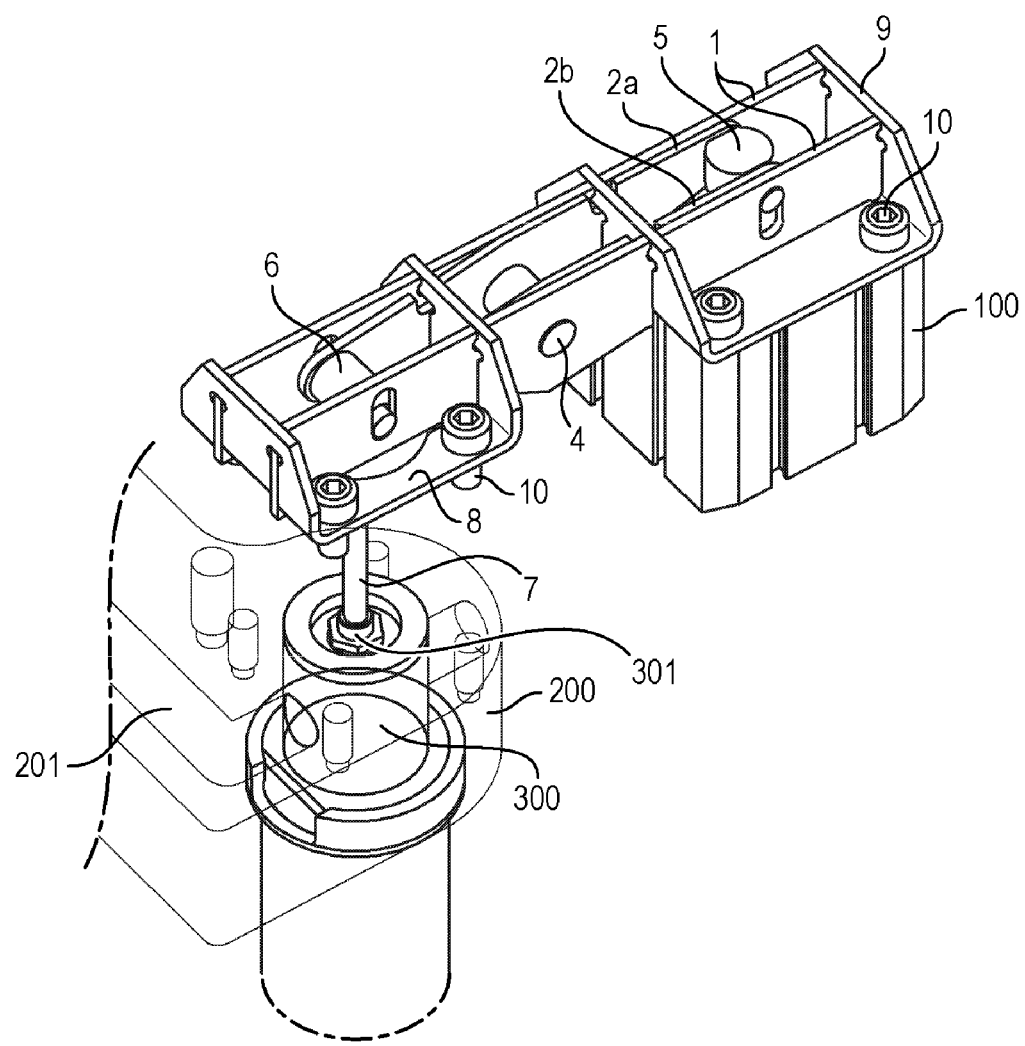
FIG. 3 illustrates the control means of FIG. 2 in the assembled position.

According to one variation and with reference to FIGS. 2 and 3, the beam is made in the form of an assembly of sheet metal structural parts 1, 8 and 9 made by cutting and bending. Two parallel arms 1, substantially symmetrical with respect to a plane perpendicular to the tilt trunnion 4, have the function of rigidly connecting a nozzle gate mount 8 and a cylinder mount 9. The arms 1 having an elongated, substantially rectangular shape, each arm has its distal end defined as the end located on the side of the cylinder, and its proximal end which is the end located on the side of the manifold.

The nozzle gate mount 8 is secured to the manifold 200 by means of four screws 10. The cylinder mount 9 is secured to one so-called upper face of the cylinder 100, perpendicular to the cylinder rod, by four screws 10. In the assembled position, the arms 1 are perpendicular to the back face of the manifold, to which is secured the nozzle gate mount 8, and to the upper face of the cylinder.

The arms 1 are connected by a tilt trunnion 4. A lever comprising two arms 2*a* and 2*b*, parallel and substanatially symmetrical with respect to a plane perpendicular to the tilt trunnion 4, has the function to transmitting the displacement of the rod of the cylinder 100 to the nozzle gate 7. For each arm 2*a*, 2*b* of the lever a distal end is defined, which is the end located on the side of the cylinder, and a proximal end which is the end located on the side of the nozzle gate. Each arm 2*a*, 2*b* has, toward its proximal end, an oblong bore 26 for admitting the trunnion 6*a* of the nozzle gate head 6. The oblong bore 26 has its greater dimension perpendicular to the sliding direction of nozzle gate 7.

Likewise, each arm 2*a*, 2*b* has toward its distal end an oblong bore 25 for admitting the trunnion 5*a* of the cylinder head 5, the greater dimension of the bore 25 being in a direction perpendicular to the nozzle gate sliding direction X. In addition, each arm 1 has oblong bores 16 and 15 for admitting the trunnions 6a and 5a respectively. The greater dimension of the oblong bores 15 and 16 is parallel to the nozzle gate sliding direction X. Thus, the greater dimension of the bores 15 and 16 determines the sliding path of the nozzle gate 7.

The nozzle gate mount 8 has generally a U shape, with a substantially square face 82 in contact with the back face of the manifold 200, and two parallel branches 83 and 84 perpendicular to the face 82. The face 82 is drilled near its corners with four bores for receiving screws 10 for mounting to the manifold 200. It also has a central cutout to allow passage of the nozzle gate head 6. In the assembled position, the branches 83 and 84 of the nozzle gate mount are perpendicular to the arm 1.

The cylinder mount 9 also has generally a U shape, with a substantially square face 92 in contact with the cylinder 199, and two parallel branches 93 and 94 perpendicular to the face 92. The face 92 is drilled near its corners with four bores for receiving screws 10 for mounting to the cylinder 100, and has a central cutout to allow passage of the cylinder head 5.

Figure 4:
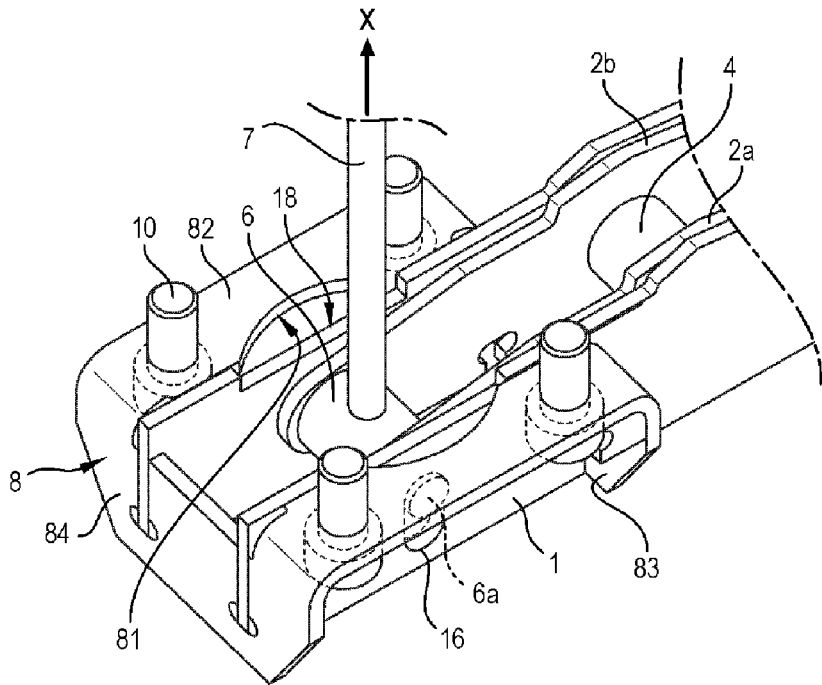
FIGS. 4 and 5 illustrate an assembly detail of the nozzle gate head in FIG. 2, in bottom and in top view respectively.

In FIG. 3 there can also be seen the manifold 200, a distribution channel 201 opening into the nozzle base 300, and the nozzle gate guide 301. The structural parts 1, 8 and 9 have cutouts advantageously defined to allow simple assembly and centering of the control means with respect to the nozzle base 300, in order to avoid any radial force from the nozzle gate 7 when it is sliding in the nozzle gate guide 301. Thus, with reference to FIG. 4, each arm 1 has, on the edge of its proximal end facing the manifold, a cutout 18 in the shape of a rectangular notch.

Figure 5:
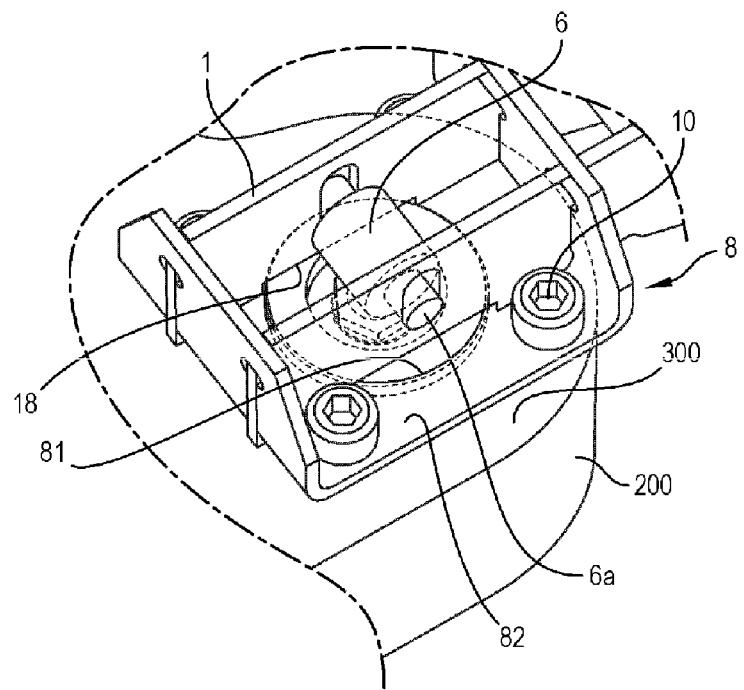

In addition, the nozzle gate mount 8 has, on its face 82 in contact with the manifold 200, a circular cutout 81 with a diameter slightly greater than that of the nozzle base 300. Thus, as can be seen in FIG. 5, the nozzle gate mount 8 and the arm 1 cap the nozzle base 300, which makes it possible to ensure good centering of the nozzle gate head 6 and the nozzle gate 7 with respect to the nozzle gate guide 301.

Figure 6:
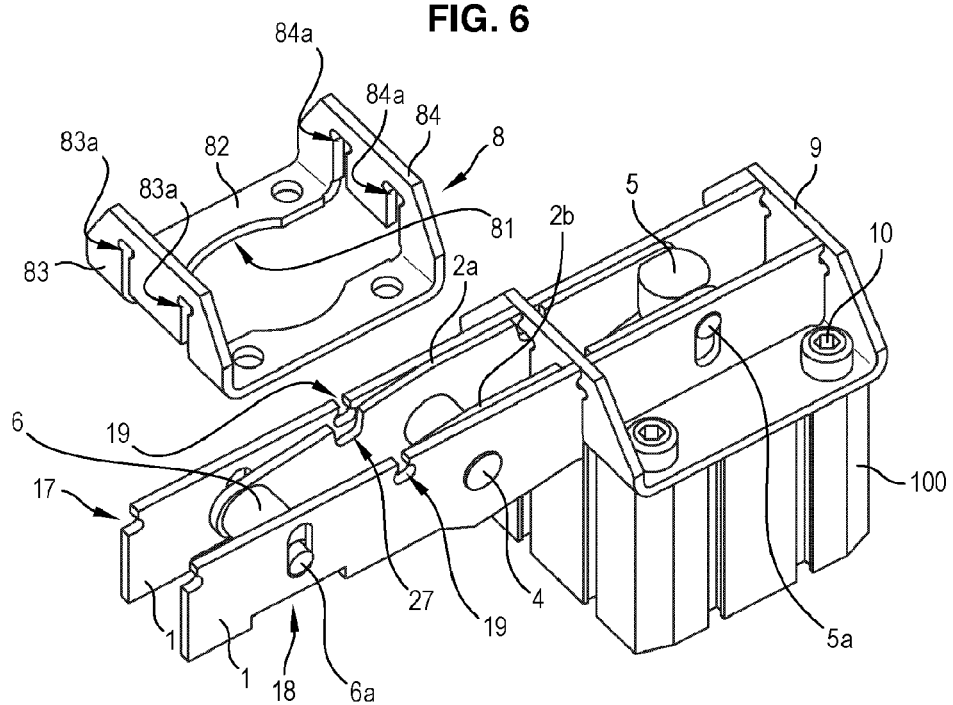
FIG. 6 illustrates the respective shapes of the beam and of the mount allowing them to interlock by cooperating shapes.

In addition, it can be seen in FIG. 6 that the mount 8 and the arm 1 have cutouts that make it possible to assemble them together by simple interlocking. Thus, the mount 8 has, on each of its branches 83 and 84, two cutouts, 83a and 84a respectively. On the branch 83, which is that located on the side of the proximal end of the arms 1, the width of the cutouts 83a is slightly greater than the thickness of each arm 1.

Figure 7:
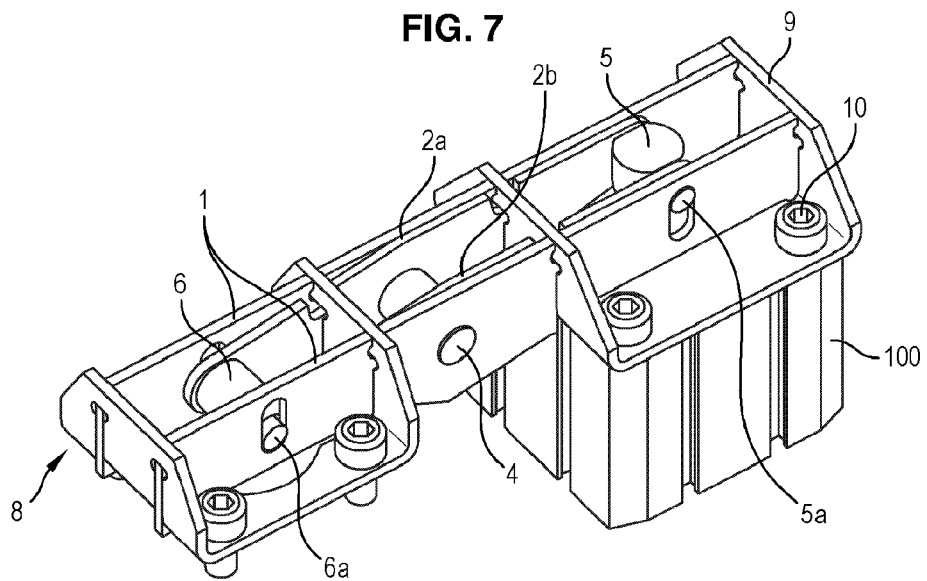
FIG. 7 illustrates the mount in FIG. 6 in the assembled position.

On the branch 84, which is that located on the side of the tilt trunnion 4, the width of the cutouts is slightly greater than the thickness of the arm 1, of the lever arm 2a or 2b, and of the clearance between them. In addition, each arm 1 has, on its edge opposite to the face of the manifold, two notches 17 and 19 for receiving the mount 8. For their part, the lever arms 2a and 2b have one cutout 27 allowing assembly of the mount 8 without interfering with the tilting of the lever. Thus it is sufficient, for assembling the mount 8, to interlock the cutouts 83a and 84a thereof with the notches 17, 19 of the arms 1 and 27 of the arms 2a and 2b, as it can be seen in FIG. 7.

The mount 9, the arms 1, 2a and 2b have cutouts similar to those which have just been described to allow the interlocking of the mount 9 with the arms 1. Preferably, the arms 1 and the arms 2a and 2b are flat. They can therefore be obtained by simply cutting them (by laser, for example) from a steel sheet including the cutouts as described above, as well as drilling the bores 16, 14, 15 and 26, 24 and 25, respectively provided to allow passage of the trunnions 6a, 4 and 5a.

The mounts 8 and 9, which have generally a U shape, are obtained by cutting from sheet steel in the flat, including making the cutouts which have just been described for interlocking on the arms 1, as well as drilling the bores for receiving the screws 10. After cutting out, the parts are folded to give them the desired U shape. Particularly advantageously, all the parts (arms 1, 2a, 2b and mounts 8 and 9) are cut from the same steel sheet, which makes the manufacturing process still simpler and more economical.

To guarantee sufficient stiffness in the structural parts, it is appropriate to select a steel sheet from 2 to 10 mm, and preferably 3 to 5 mm thick. The beam thus formed and illustrated in FIG. 3 has a width of about 70 mm, a length on the order of 180 mm and a height of 30 mm. The cylinder is for example a pneumatic cylinder, 60 mm high for example. Of course, these dimensions are only given by way of non-limiting examples. It is emphasized that the use of sheet metal parts allows better dissipation of the heat that is liable to be transmitted to the cylinder.

The order of assembly of the control means of the nozzle gate is the following:
(a) assembly of the nozzle gate head 6 to the nozzle gate 7, the same first being inserted into the nozzle gate guide 301;
(b) assembly of the cylinder head 5 on the rod of the cylinder 100;
(c) interlocking a first arm 2a and a first arm 1 onto the trunnions 6a and 5a of the nozzle gate head 6 and of the cylinder head 5;
(d) positioning of the tilting trunnion 4 in the bores 24 and 14 of the first arm 2a and of the first arm 1;
(e) positioning of the second arm 2b and of the second arm 1 on the trunnions 6a, 4 and 5a;
(f) interlocking the cylinder mount 9 with the arms and driving the four screws 10 into the cylinder 1;
(g) interlocking the nozzle gate mount 8 with the arms 1 and driving the four screws 10 into the manifold 200.

It will be understood, however, that this order is given only by way of an example and that a different sequence of steps can be contemplated. The fabrication and the assembly of this new device are therefore particularly simple and inexpensive. This new device thus makes it possible to significantly reduce the acquisition price of the control means.

Finally, it is self-evident that the examples just given are only particular illustrations and in no way limiting as to the fields of application of the invention. In particular, other forms of the solid beam, of the lever arms, of the structural parts and of the cutouts allowing them to be interlocked can be contemplated without thereby departing from the scope of the present invention. Likewise, other methods of assembling the cylinder to the beam, the beam to the manifold and the parts making up the beam when it is not solid, can be employed. Additionally, the system illustrated here includes only one injection nozzle, but it is understood that the invention applies equally to a system including a plurality of injection nozzles, each equipped with a nozzle gate and with control means for said nozzle gate.

The invention claimed is:
1. A system for injecting a thermoplastic material in the fluid state into a molding cavity, the system comprising:
   a manifold operably held at an injection temperature greater than the final temperature beyond which the material occurs in the fluid state, the manifold including a distribution channel and at least one thermoplastic material outlet;
   an injection nozzle defining at least one portion of a transit passage an entrance of which is fluidically connected with the outlet of the distribution channel, and an outlet of the transit passage opening substantially into the molding cavity;

a nozzle gate mounted within the transit passage so as to slide between a position closing same and a position opening same;

a power cylinder operably causing the nozzle gate to slide alternately;

the power cylinder including a rod parallel to a sliding direction (X) of the nozzle gate, secured in an offset fashion to the manifold through a flattened beam, and a lever arranged to tilt about a trunnion so as to transmit to the nozzle gate the movements of the cylinder rod.

2. The system of claim 1, wherein the beam holds the tilting trunnion of the lever.

3. The system of claim 1, wherein the beam is a solid part.

4. The system of claim 1, wherein the beam is made up of an assembly of parts made of sheet steel.

5. The system of claim 4, wherein the beam includes two parallel arms, a cylinder mount secured to the cylinder, and a nozzle gate mount secured to the manifold.

6. The system of claim 5, wherein the arms and the nozzle gate and cylinder mounts have complementary cutouts allowing them to interlock.

7. The system claim 5, wherein the arms and the nozzle gate mount have cutouts allowing them to be centered on the nozzle base.

8. The system of claim 4, wherein the lever includes two arms made of sheet steel.

9. The system of claim 4, wherein the thickness of the sheet metal parts is between 2 and 10 mm.

10. A sliding control device for a nozzle gate of an injection valve for an injection system, the device comprising:

a flattened beam holding a power cylinder in an offset position on a manifold; and a lever arranged so as to tilt about a trunnion so as to transmit to the nozzle gate the movements of a rod of the cylinder.

11. A manufacturing method for the system of claim 4, comprising:

(a) cutting out and, if necessary, bending of the parts making up the beam;

(b) assemblying the parts and of the lever; and (c) securing of the assembly to the cylinder and the manifold.

12. The method of claim 11, wherein step (a) also includes cutting out the lever arms.

13. The method of claim 11, wherein step (a) includes laser cutting.

14. The method of claim 11, wherein step (b) is carried out by interlocking the parts.

15. An injection molding system comprising:

a pivot;

an elongated member tiltable about the pivot;

a nozzle gate coupled to the elongated member and being linearly moveable in response to the tilting thereof; and an elongated arm also tiltable about the pivot, ends of the arm being coupled to the elongated member to allow some relative movement therebetween, the arm and member being parallel in at least one position.

16. The system of claim 15, further comprising a second elongated arm tilting about the pivot, the arms being substantially symmetrical but spaced apart from each other, the arms being coupled to the elongated member by pin-and-slot configurations adjacent the ends of the arms.

17. The system of claim 15, wherein the elongated member is a beam including multiple sheet metal components assembled together.

18. The system of claim 15, wherein the elongated member is a beam having a metallic monobloc configuration with multiple internal openings between ends of the beam, further comprising threaded fasteners being affixed in at least some of the openings for securing a manifold to the beam.

19. The system of claim 15, further comprising a nozzle gate head entirely located inside parallel outer walls of the elongated member, the nozzle gate being attached to the nozzle gate head.

20. The system of claim 15, further comprising a laterally enlarged mount, connected to the elongated member, including a cutout located entirely internal to peripheral lateral edges thereof, and a portion of the nozzle gate extending through the cutout.

* * * * *